(12) United States Patent
Bukowski et al.

(10) Patent No.: US 8,518,458 B2
(45) Date of Patent: Aug. 27, 2013

(54) TEA-DERIVED COMPOSITIONS AND METHODS OF USING SAME FOR CARDIOVASCULAR HEALTH

(75) Inventors: Jack F. Bukowski, Marboro, MA (US); Jeffrey Walters, Winter Park, FL (US)

(73) Assignee: Immune Guard, LLC, Ft. Pierce, FL (US)

( * ) Notice: Subject to any disclaimer, the term of this patent is extended or adjusted under 35 U.S.C. 154(b) by 1385 days.

(21) Appl. No.: 11/672,547

(22) Filed: Feb. 8, 2007

(65) Prior Publication Data

US 2008/0081066 A1   Apr. 3, 2008

Related U.S. Application Data

(60) Provisional application No. 60/826,451, filed on Sep. 21, 2006.

(51) Int. Cl.
*A01N 65/00* (2009.01)
(52) U.S. Cl.
USPC .......................................................... 424/725
(58) Field of Classification Search
None
See application file for complete search history.

(56) References Cited

U.S. PATENT DOCUMENTS

| | | | | |
|---|---|---|---|---|
| 6,831,103 | B1 * | 12/2004 | Ueda et al. ................... | 514/563 |
| 7,241,461 | B2 * | 7/2007 | Myhill et al. ................. | 424/729 |
| 2002/0151506 | A1 * | 10/2002 | Castillo et al. ................. | 514/27 |
| 2008/0057161 | A1 * | 3/2008 | Brucker et al. ................. | 426/73 |

FOREIGN PATENT DOCUMENTS

| | | | |
|---|---|---|---|
| JP | 05229938 | * | 9/1993 |
| WO | WO0149285 | | 7/2001 |
| WO | WO2004093865 | | 11/2004 |

OTHER PUBLICATIONS

Life extension, 5 pages, 2009.*
Jaga silk, 3 pages, 2009.*
Japan Green tea .com, 3 pages, 2009.*
The world's healthiest food, 33 pages, 2010.*
Green tea benefits, 4 pages, 2010.*
Yokogoshi et al., "Reduction Effect of Theanine on Blood Pressure and Brain 5-Hydroxyindoles in Spontaneously Hypertensive Rats", Biosci, Biotech, Biochem. 1995, vol. 59(4) pp. 615-618.
WPI/Thomson CN20041018206, 2006, (XP-002660877) Abstract "Health Food Stabilsed Adjust Blood Pressure Improve Sleep Preparation Method".
Lin and Lin-Shiau, "Mechanisms of hypolipidemic and anti-obesity effects of tea and tea polyphenols" Mol. Nutr, Food Res, 2006, vol. 50, pp. 211-217.
Weisburger and Chung, "Mechanisms of chronic disease causation by nutritional factors and tobacco products and their prevention by tea polyphenols" Food and Chemical Toxicology, 2002, vol. 40, pp. 1145-1154.
Chow et al., "Pharmacokinetics and safety of green tea polyphenols after Multiple-Dose Administration of Epigallocatechin Gallate and Polyphenon E in Healthy Individuals", Clinical Cancer Research, vol. 9, pp. 3312-3319.

* cited by examiner

*Primary Examiner* — Michael Meller
(74) *Attorney, Agent, or Firm* — Timothy H. Van Dyke; Beusse, Wolter, Sanks, Mora & Maire, P.A.

(57) ABSTRACT

Disclosed herein are compositions comprising tea derived components which are useful in decreasing elevated blood pressures, lowering LDL and/or lowering inflammatory markers of cardiovascular disease. Specifically exemplified herein are compositions comprising predetermined amounts of L-theanine and EGCG, and methods of using same to improve cardiovascular health.

1 Claim, 4 Drawing Sheets

Serum amyloid alpha
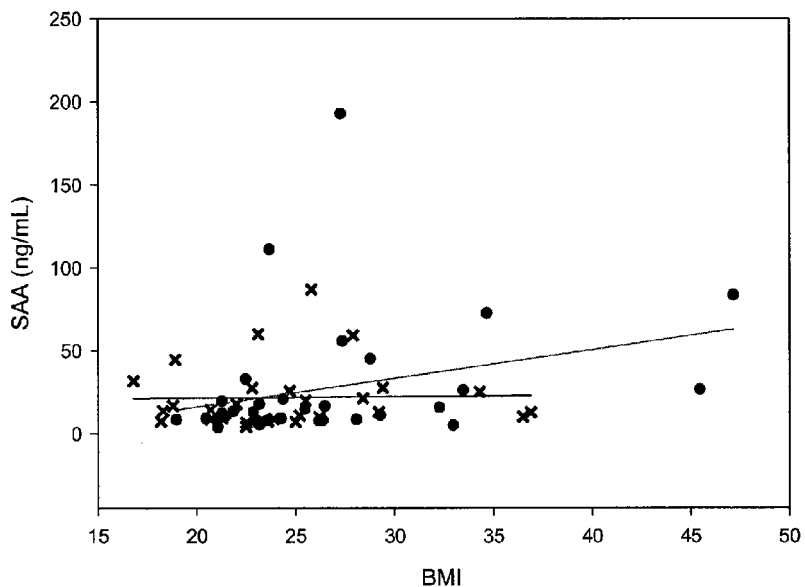
Figure 4
4a
SAA versus age
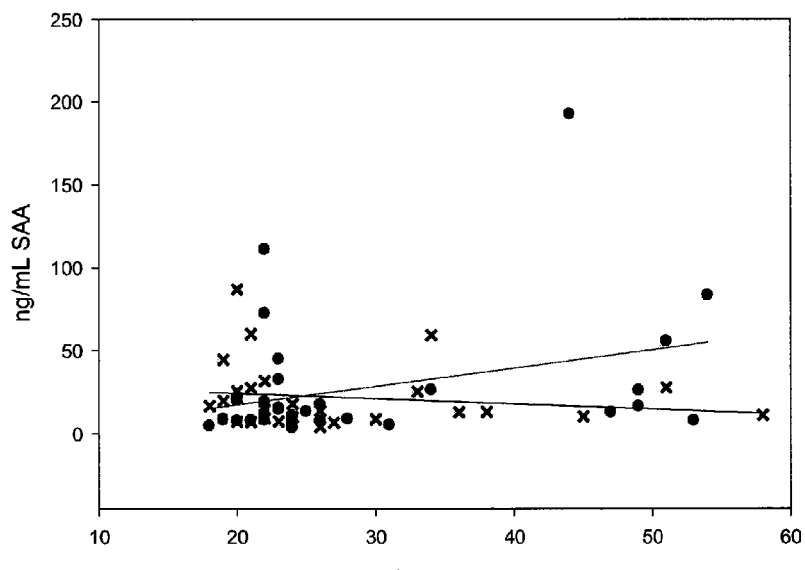
4b

TEA-DERIVED COMPOSITIONS AND METHODS OF USING SAME FOR CARDIOVASCULAR HEALTH

CROSS-REFERENCE TO RELATED APPLICATION

This application is related to U.S. Provisional Patent Application 60/826,451; filed Sep. 21, 2006 to which priority is claimed under 35 USC §119.

INTRODUCTION

For centuries, tea beverage has been linked to good health. Most studies have been observational, showing benefit in cardiovascular (CV), anti-aging, neurodegenerative, anti-cancer, and bone areas [1, 2]. There are numerous other studies consistent with no health benefits [3, 4]. These studies, both positive and negative, are fraught with confounding variables that are inherent in observational studies employing free-living human beings as subjects. Such studies are further complicated by the nature of tea beverage. There are hundreds of varieties of the tea species, Camellia sinensis, and numerous ways to process tea that can lead to different components in a cup of tea [5, 6]. Storing and brewing methods lead to further variability that is difficult to standardize, as does the use of milk and lemon [7, 8]. Another obvious source of conflict is that there is no general agreement on what quantity constitutes a cup of tea. Thus, it is not surprising that the results of many published trials conflict with one another.

Hypertension is a well-know risk factor for CVD. Studies on the effects of tea drinking tea extract ingestion and chronic hypertension have shown not shown significant effects [9] [10]. This lack of effect may be due to the presence of caffeine, and/or the absence of L-theanine. However, neither catechins nor L-theanine separately or together has been shown to reduce blood pressure in humans, though L-theanine reduces blood pressure in spontaneously hypertensive rats [11, 12], and catechin mixtures including epigallocatechin gallate (EGCG) relax vascular smooth muscle cells [13].

An elevated level of LDL cholesterol is another well-known risk factor for CVD. There are several clinical trials showing that drinking green tea enriched for theaflavins or black tea containing theaflavins decreases LDL cholesterol [14-16]. Recent studies [17, 18] showed that drinking green tea lowers LDL cholesterol. Possible mechanisms for catechins lowering LDL cholesterol include increased synthesis by liver cells of the receptor for LDL [19], and inhibition of squalene epoxidase, a rate-limiting step in cholesterol biosynthesis [20].

Elevated levels of serum amyloid alpha (SAA) and C-reactive protein (CRP), markers of chronic inflammation, are independent risk factors for CV disease [21-23]. Two recent studies have shown that drinking tea is associated with decreases in CRP and SAA [24, 25].

EGCG is highly anti-inflammatory. EGCG inhibits the production of pro-inflammatory mediators such as chemokines [26, 27], prostaglandins [27], and tumor necrosis factor (TNF) [28]. EGCG also inhibits adhesion molecule expression [29], MAP kinases [30], and neutrophil migration [31].

SUMMARY

The subject invention is based on the inventors surprising discovery that compositions containing enriched amounts of certain tea components, namely L-theanine and EGCG, is a safe and effective supplement for reducing blood pressure, LDL cholesterol, and chronic inflammation. Through a randomized, double-blind, placebo-controlled interventional study using compositions containing these key tea components (Camellia sinensis composition; CSC) with a primary endpoint of lowering blood pressure, lowering LDL and lowering inflammatory markers of CRP and SAA, the inventors have discovered that L-theanine and EGCG work together to generate surprising, unexpected, results of lowering key risk factors for cardiovascular disease.

BRIEF DESCRIPTION OF THE DRAWINGS

FIG. 4. Regression analysis. The red line represents placebo subjects, and the black line represents CSC subjects. Serum amyloid alpha (SAA) is known to increase with body mass index (BMI) and also with age. In placebo subjects, SAA increases with increasing BMI, but in CSC subjects, there is no such increase (upper panel, 4a). In placebo subjects, SAA increases with increasing age, but in CSC subjects, there is no such increase (lower panel, 4b). These data demonstrate that the CSC works as an anti-aging composition.

DETAILED DESCRIPTION

Figure 1:
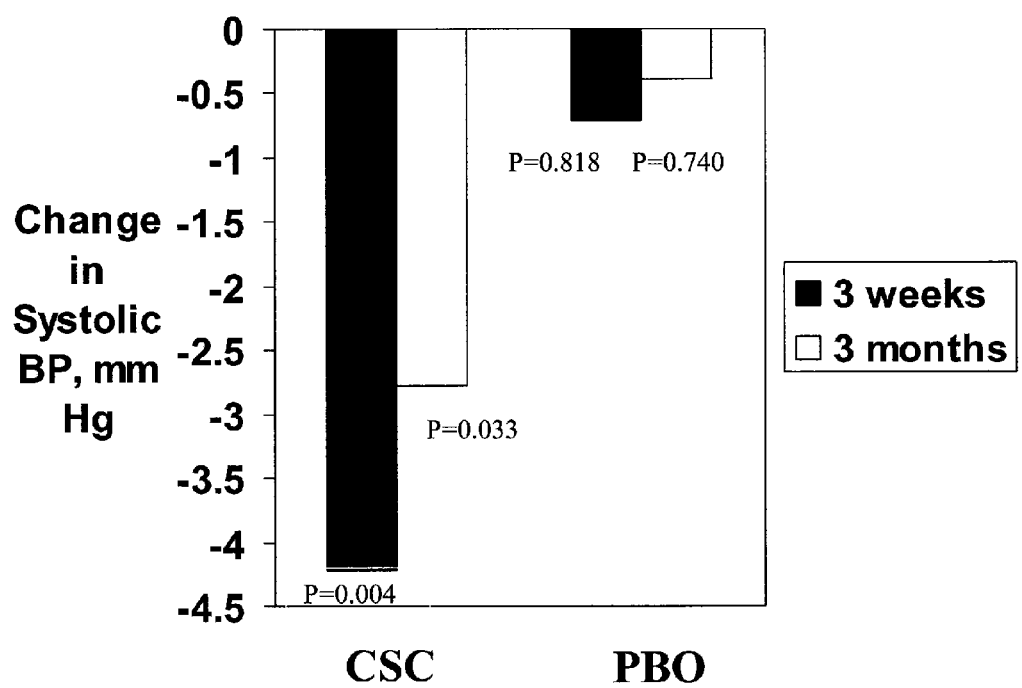
FIG. 1. Change in systolic blood pressure. Blood pressure was measured before and either three weeks or three months after taking either CSC (Camellia sinensis formula) or placebo (PBO). Shown are the differences from baseline.
Figure 2:
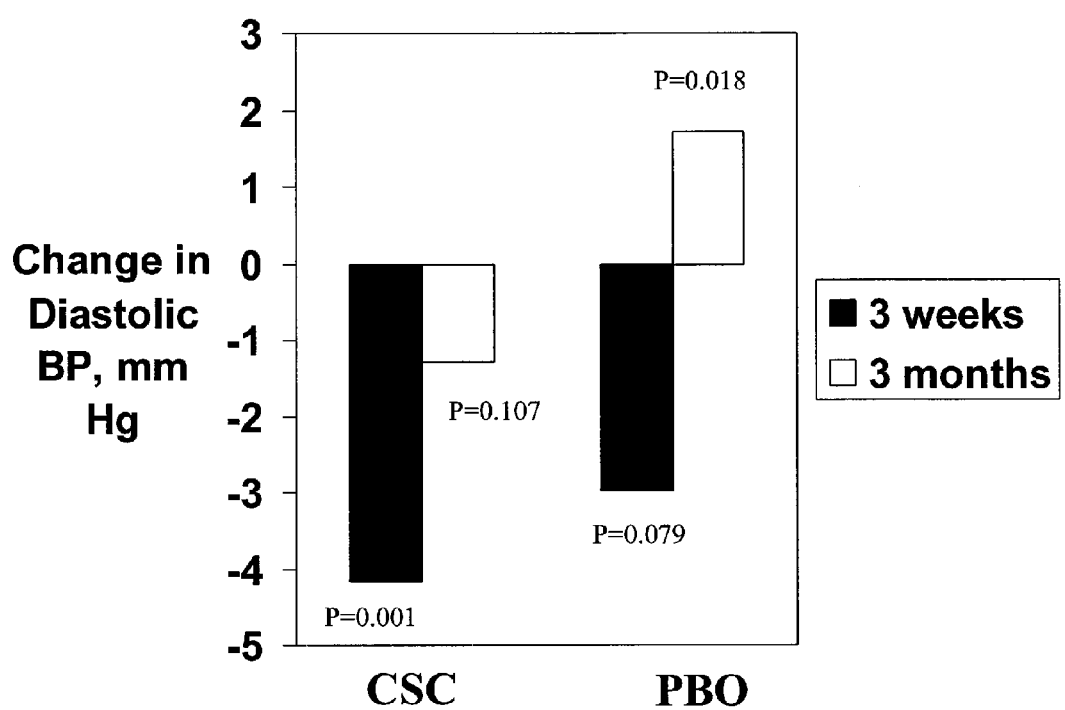
FIG. 2. Change in diastolic blood pressure. Blood pressure was measured before and either three weeks or three months after taking either CSC (Camellia sinensis formula) or placebo (PBO). Shown are the differences from baseline.

L-theanine, abundant in tea, is catabolized in the body to yield ethylamine, which appears in the blood of rats given L-theanine, and has been shown to appear in the urine of tea drinkers. Tea extraction procedures normally exclude amino acids, including L-theanine. Compositions taught herein are unique in that they intentionally combine L-theanine and an EGCG in enriched amounts.

The EGCG composition is procured from tea and comprises between 10-100 percent EGCG, by weight. In optimal embodiments, the EGCG comprises at least 40 to 50 percent EGCG, by weight. It is known that EGCG procured from tea can contain caffeine. U.S. Pat. No. 7,012,149 is cited for background on procuring EGCG containing composition. Also commercially available products such as SUNPHENON® line of products from Taiyo International, Minneapolis, Minn. offer EGCG compositions may be used in accordance with the teachings herein.

In preferred embodiments caffeine is reduced or eliminated from the EGCG composition either before or after procurement of the EGCG composition. The inventors have found that reducing the caffeine amount provides a novel composition with increased compliance. Caffeine intake can cause a number of adverse side effects, including, but not limited to, excitability in children, constipation, nervousness, dizziness, hypertension, and arrythmias. For certain embodiments, the inventors have realized that compositions may be particularly marketed to schools for use in beverages and food served to students. Schools can be a primary source epicenter of virus origination and distribution. The administration of compositions taught herein will serve to reduce or slow the spread of microbial infections. A composition containing caffeine would not be appropriate for such application.

The procurement of L-theanine is separate from tea polyphenols. Accordingly, an L-theanine composition is obtained from tea where the L-theanine composition comprises between 10-100 percent L-theanine. This L-theanine composition may be admixed with the EGCG containing tea polyphenol composition. See U.S. Pat. No. 6,831,103 for background on procurement of L-theanine.

Theanine may be a glutamic acid derivative (γ-glutamylethylamide), which is an amino acid component naturally contained largely in tea-leaves. Methods for preparing theanine used in the present invention may include, for instance, a method of extracting from tea-leaves; an organic synthesis method [Chem. Pharm. Bull, 19(7), 1301-1307 (1971)]; a method of treating a mixture of glutamine and ethylamine with glutaminase (Japanese Unexamined Patent Publication No. Hei 7-55154); a method comprising culturing cultured cells of tea in a medium containing ethylamine, thereby achieving growth promotion of the cultured cells while increasing the cumulative amount of theanine in the cultured cells (Japanese Patent Laid-Open No. Hei 5-123166); modification methods in which ethylamine is substituted by an ethylamine derivative such as ethylamine hydrochloride in the methods disclosed in Japanese Unexamined Patent Publication No. Hei 7-55154 or Japanese Patent Laid-Open No. Hei 5-123166; and the like, and any of the methods may be used. The above-mentioned "tea-leaves" include green tea-leaves, oolong tea-leaves, black tea-leaves, and the like.

Theanine can be used as any of L-theanine, D-theanine and DL-theanine. Among them, the L-form is preferred in the present invention, because the L-form is approved as a food additive, and is economically utilizable. In addition, theanine used in the present invention may be in any forms, such as purified products, crudely purified products and extracts. Also, a commercially available product [SUNTHEANINE (registered trade mark), manufactured by Taiyo Kagaku Co., Ltd.] may be used.

According to one embodiment, the invention pertains to a method of lowering blood pressure in a subject in need thereof comprising orally administering a composition comprising L-theanine and EGCG, wherein said composition is administered according to a dosage amounting to at least 25 mg of L-theanine and 25 mg EGCG per day. In a specific embodiment at least 200 mg of L-theanine is administered per day. In a further embodiment at least 150 mg of L-theanine is co-administered with at least 125 mg of EGCG per day. In a particular embodiment, between 180 to 220 mg of L-theanine and between 180 to 220 mg of EGCG is administered per day. In alternative embodiments, the daily amount of EGCG that is used to combine with L-theanine is from about 200 mg to 450 mg. In specific embodiment EGCG is provided at up to 800 mg of 45 percent EGCG composition.

Pre-hypertension has been defined as a SBP in the range of from 120 mmHg to 139 mmHG and/or a DBP in the range of from 80 mmHg to 89 mmHg. Pre-hypertension is considered to be a precursor of hypertension and a predictor of excessive cardiovascular risk (Julius, S., et al., *N. Engl. J. Med.,* 354: 1685-1697 (2006)). Hypertension, or elevated BP, has been defined as a SBP of at least 140 mmHg and/or a DBP of at least 90 mmHg.

According to another method, the present invention relates to a method of treating pre-hypertension in a subject in need of treatment thereof comprising administering to the subject a therapeutically effective amount of CSC comprising an admixture of an L-theanine composition comprising at least 10-100 percent L-theanine and a tea polyphenol composition comprising at least 10-100 percent EGCG. A subject receiving treatment for pre-hypertension pursuant to the above-described method has a systolic blood pressure in a range of 120 mmHg to 139 mmHg, a diastolic blood pressure in the range of 80 mmHg to 89 mmHg or a combination of a systolic blood pressure in a range of 120 mmHg to 139 mmHg and a diastolic blood pressure in the range of 80 mmHg to 89 mmHg.

In yet still another embodiment, the present invention relates to a method of decreasing pre-hypertension blood pressure or elevated blood pressure in a subject comprising administering to the subject a therapeutically effective amount of CSC comprising an admixture of an L-theanine composition comprising at least 10-100 percent L-theanine and a tea polyphenol composition comprising at least 10-100 percent EGCG. A subject being treated pursuant to this method can have a pre-hypertension blood pressure that comprises a systolic blood pressure in the range of 120 mmHg to 139 mmHg, a diastolic blood pressure in the range of 80 mmHg to 89 mmHg or a combination of a systolic blood pressure in the range of 120 mmHg to 139 mmHg and a diastolic blood pressure in the range of 80 mmHg to 89 mmHg. A subject being treated pursuant to this method can have an elevated blood pressure that comprises a systolic blood pressure of at least 140 mmHg, a diastolic blood pressure of at least 90 mmHg, a mean arterial pressure of at least 106 mmHg or a combination of a systolic blood pressure of at least 140 mmHg and a diastolic blood pressure of at least 90 mmHg. For example, the subject may have an elevated blood pressure comprising a systolic blood pressure of at least 160 mmHg or a diastolic blood pressure of at least 95 mmHg. The administration of the at least one compound pursuant to this method can lower the systolic blood pressure, the diastolic blood pressure, the mean arterial pressure or a combination of the systolic blood pressure and diastolic blood pressure of the subject.

According to another embodiment, the invention pertains to a capsule or tablet or liquid suspension comprising a combination of L-theanine and EGCG, wherein the capsule or table comprises between 10 percent to 100 percent, by weight, L-theanine and between 10 percent to 100 percent, by weight EGCG. In a specific embodiment, the capsule or tablet comprises between 15 percent to 65 percent L-theanine and 15 percent to 65 percent EGCG. In a further embodiment, the capsule or tablet or suspension comprises between 30 percent to 60 percent, by weight, tea polyphenols. In a specific embodiment, the capsule or table or suspension is decaffeinated. In an alternative embodiment, the capsule or tablet may contain sulphoraphane (from 5-50 mg per day).

The tablet or capsule may be, but is not limited to, from 10 to 500 mg total weight. In specific embodiments, the capsules are 25, 50, 75, 100, 125, 150, 175, 200, 225, 250, 275, 300, 325, 350, 375, 400, 425, 450, 475, or 500 mg, total individual weight.

According to another embodiment, the invention pertains to reducing LDL in a subject in need thereof comprising orally administering a composition comprising L-theanine and EGCG, wherein said composition is administered according to a dosage amounting to at least 25 mg of L-theanine and 25 mg EGCG per day. In a specific embodiment at least 100 mg of L-theanine is administered per day. In a further embodiment at least 115 mg of L-theanine is co-administered with at least 100 mg of EGCG per day. In a particular embodiment, between 150 to 600 mg. of L-theanine and between 150 to 600 mg of EGCG is administered per day. Generally, subjects who have LDL levels of >100 mg/dl are considered to have elevated LDL levels and a higher risk of heart disease. Accordingly, the population of subject having higher than 100 mg/dl LDL are believed to have the most benefit by this method embodiment.

With regard to cholesterol levels, there are several subpopulations of subjects that could particularly benefit from administration of CSC embodiments described herein include but are not limited to the following. The first has an LDL cholesterol >100 but cannot tolerate or does not want to take a statin. Another is such a patient who takes a CSC embodiment as an adjunct therapy due to a poor result from a statin. Another is a patient who has an LDL below a hundred but not below 70, who has one or more additional cardiac risk factors, including but not limited to hypertension, high SAA or CRP levels, obesity, smoking, positive family history of adverse CV event. Yet another is a patient who has achieved his/her target LDL around 70 with statins, and wants to stop statins and try maintaining with HeartGuard. It is contemplated that the foregoing subjects would be included in the group of subjects in need of a CSC embodiment as described herein.

The treatment of prehypertension and hypertension has been described above. In addition to the subjects who have a blood pressure as defined above for prehypertension or hypertension other factors can be considered in determining those patients who would particularly benefit from a CSC embodiment described herein. Subjects who may have an SBP>140 and/or a DBP>90, but cannot tolerate or do not want to take a pharmaceutical anti-hypertensive; subjects who experience a poor result from a pharmaceutical anti-hypertensive and could take a CSC as an adjunct therapy; subjects who have a SBP>120 and/or a DBP>80 with one or more additional cardiac risk factors, including but not limited to hypertension, high SAA or CRP levels, obesity, smoking, positive family history of adverse CV event, and/or subjects who have achieved SBP<120 and DBP<80 but who desire ceasing pharmaceutical anti-hypertensives comprise subpopulations of subjects who could particularly benefit from administration of a CSC embodiment and would be included in the group of subjects in need of such administration.

With regard to elevated SAA or CRP, a subject having a SAA or CRP that is above the upper limit of normal, and may or may not have other cardiac risk factors or be taking other medications to control those other risk factors would be a particularly good candidate for administration of a CSC embodiment.

As described herein certain embodiments pertain to an admixture of 2 active ingredients, (L-theanine and EGCG) that have been clinically proven in this combination to decrease SBP and DBP, SAA, and LDL cholesterol. Neither ingredient alone nor together has been shown to have this range of activity against these cardiovascular risk factors.

According to another embodiment, the invention pertains to lowering CRP and/or SAA levels in a subject comprising orally administering a composition comprising L-theanine and EGCG, wherein said composition is administered according to a dosage amounting to at least 25 mg of L-theanine and 25 mg EGCG per day.

In a specific embodiment, the composition is orally administered as a beverage comprising water, flavoring, EGCG composition, and L-theanine, wherein said beverage is administered according to a dosage amounting to at least 25 mg of L-theanine a day and at least 25 mg of EGCG composition a day. In a specific embodiment at least 100 mg of L-theanine is administered per day. In a further embodiment at least 120 mg of L-theanine is co-administered with at least 125 mg of EGCG per day. In a specific embodiment, between 150 to 600 mg. of L-theanine and between 150 to 600 mg of EGCG is administered per day.

For certain method embodiments, the dosage of L-theanine is at least 25 mg per day. The dosage of L-theanine is typically between 25-600 mg of L-theanine a day, but may be higher than 600 mg. In certain embodiments, the dosage of L-theanine is or about 25, 50, 75, 100, 125, 150, 160, 170, 180, 190, 200, 210, 220, 230, 240, 260, 280, 300, 320, 340, 360, 380, 400, 420, 440, 460, 480, 500, 520, 540, 560, 580 or 600 mg of L-theanine a day. In a specific embodiment, the dosage is such that about 200 mg L-theanine is provided per day. The dosage of EGCG is at least 25 mg per day. The dosage of EGCG is typically between 25-600 mg of EGCG a day. In certain embodiments, the dosage of L-theanine is or about 25, 50, 75, 100, 125, 150, 160, 170, 180, 190, 200, 210, 220, 230, 240, 260, 280, 300, 320, 340, 360, 380, 400, 420, 440, 460, 480, 500, 520, 540, 560, 580 or 600 mg of L-theanine a day. In a specific embodiment, the dosage is such that about 200 mg L-theanine is provided per day.

In another embodiment, the subject invention is directed a composition comprising an admixture of an L-theanine composition and a decaffeinated tea polyphenol composition, wherein said L-theanine composition comprises at least 50 percent L-theanine and said decaffeinated tea polyphenol composition comprises at least 30 percent EGCG, wherein said L-theanine composition and tea polyphenol composition are present in a ratio of 2:1, 1.9:1, 1.8:1, 1.7:1, 1.6:1, 1.5:1, 1.4:1, 1.3:1, 1.2:1, 1:1, 1:1.1, 1:1.2, 1:1.3, 1:1.4, 1:1.5, 1:1.6, 1:1.7, 1:1.8, 1:1.9, 1:2, or 1:3 respective to each other. In a related embodiment, the composition is used as a food additive. In a specific embodiment, the composition comprises between 10 percent to 80 percent, by weight, L-theanine and between 10 percent to 80 percent, by weight EGCG. In a specific embodiment, the capsule or tablet comprises between 15 percent to 65 percent L-theanine and 15 percent to 65 percent EGCG. In a more specific embodiment, the composition comprises between 20 percent to 40 percent L-theanine and 20 percent to 40 percent EGCG.

In yet another embodiment, the subject invention pertains to a food product comprising a therapeutically effective amount of L-theanine and EGCG. In a specific embodiment, the invention relates to a food product comprising at least 25 mg of a L-theanine and tea polyphenol composition, such as, but not limited to, the composition described in the preceding paragraph. Examples of food products may include, but are not limited to, energy bars, sauces, salad dressings, frozen dinners, chips, canned soups, yoghurt, cereals, bread, flour and grains. In an alternative but related embodiment, the subject invention pertains to a packaged food product having a total weight of between 25 mg to 50 kg. The packaged food product comprises at least 0.1 percent by weight L-theanine and at least 0.1 percent by weight EGCG. In a specific embodiment, the food product comprises between about 0.1-10 percent, by weight, L-theanine and between about 0.1 to 10 percent, by weight, EGCG. In other embodiments, the amount of L-theanine and EGCG are at least 25 mg per serving.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described.

Those skilled in the art of medicinal chemistry and pharmaceutical formulations will appreciate that other formulations can be devised for appropriate oral, parenteral or other administration. U.S. Pat. Nos. 6,821,532 and 7,157,493 are cited for general background of pharmaceutical formulations.

Example 1

EGCG/L-Theanine Formulation Embodiment

According to a specific embodiment, the invention pertains to a capsule comprising an admixture of or about 25-300 mg of an at least 95 percent L-theanine containing composition and of or about 50-400 mg of a decaffeinated tea polyphenol composition containing at least 45 percent EGCG. In a more specific embodiment, the subject invention pertains to a capsule comprising 300 mg of an admixture comprising 100 mg of a 98 percent L-theanine containing composition and 200 mg of a 50 percent EGCG containing tea polyphenol composition.

Example 2

Cardiovascular Health Improving Beverage

According to another embodiment, the invention pertains to an article of manufacture comprising a beverage comprising water, flavoring, EGCG composition, and L-theanine and a container in which the beverage is disposed. In certain embodiments, the container volume may be in the range of between 25 ml to 5000 ml. The article of manufacture comprises at least 25 mg of L-theanine and at least 25 mg of EGCG. In a preferred embodiment, the article of manufacture comprises at least 50 mg of L-theanine and at least 50 mg of EGCG. In a specific embodiment, the article of manufacture comprises at least 75 mg, 100 mg, 125 mg, 150 mg, 175 mg, 200 mg 225 mg or 250 mg of EGCG and at least 75 mg, 100 mg, 125 mg, 150 mg, 175 mg, 200 mg 225 mg or 250 mg mg of L-theanine. The EGCG composition is procured from tea and comprises between 10-100 percent EGCG, by weight. In optimal embodiments, the EGCG comprises at least 40 to 50 percent EGCG, by weight. It is known that EGCG procured from tea can contain caffeine. In preferred embodiments caffeine is reduced or eliminated from the EGCG composition either before or after procurement of the EGCG composition. The procurement of L-theanine is separate from tea polyphenols. Accordingly, an L-theanine composition is obtained from tea where the L-theanine composition comprises between 10-100 percent L-theanine. This is admixed with the EGCG containing tea polyphenol composition. Flavorings pertain to any substance that is used to modify, enhance or mask flavors. Flavors can include but are not limited to sweeteners, salts, flavor substances, acidulents. Sweetener includes both natural and artificial sweeteners. Sweeteners include, but are not limited to, sucralose, acesulfame potassium, aspartame, saccharin, sucrose, glucose, fructose, high fructose corn syrup, invert sugars, sugar alcohols including sorbitol, mannitol and mixtures thereof. As used herein, the term "acidulents" includes, but is not limited to, citric acid, lactic acid, malic acid, sodium citrate, potassium citrate. As used herein, the term "preservatives/antimicrobial agents" includes, but is not limited to sodium benzoate, potassium benzoate, benzoic acid, ethylparaben, methylparaben, propylparaben, sorbic acid.

Examples of beverages include, but are not limited to, fruit juice mixed with the L-theanine/EGCG composition, a "smoothie" (fruit juice and blended fruit) with L-theanine/EGCG composition provided therein, fitness drinks, such as GATORADE®, POWERADE®, etc. with composition provided therein, tea drinks with composition added therein, and sodas with composition added therein.

Example 3

Double Blind Placebo Study

Materials and Methods

Subjects. Healthy men (n=52) and women (n=72) between 21 and 70 (mean=29) years of age were recruited to participate in a 12-wk randomized, double-blind placebo controlled parallel study. Subjects were recruited from the University of Florida campus, and the Gainesville, Fla. community, during January of 2006. The University of Florida Institutional Review Board approved the study protocol, and informed written consent was obtained from each subject. Screening for the study occurred by telephone and/or personal interviews. Exclusion criteria consisted of the following: had not had a cold in the past two years; vegetarian diet; steroids; chemotherapy or other immune suppressing therapy within the last year; chronic antibiotics or other infectious disease preventative; chronic illness; recent surgery or illness; pregnant and/or lactating females. Also excluded were those who daily consumed: greater than one cup (250 mL) of tea; an average of seven or more servings of fruits and vegetables; herbal supplements, vitamins other than a multivitamin or vitamin D. The study was conducted from January through May of 2006. Participants were in contact with the enrolling research assistant by e-mail and telephone throughout the study, and returned to fill out an exit questionnaire upon study completion. Overall study compliance was monitored through the exit questionnaire and by enumeration of remaining capsules in returned bottles at the end of then study [32].

Study Protocol. The study was conducted from January through May of 2006. Subjects were randomly assigned to supplement and placebo groups. Both subjects and investigators were blinded as to the treatments. HeartGuard, LLC (Orlando, Fla.) provided HeartGuard®, an embodiment of a *Camellia sinensis* composition (CSC) and placebo capsules. This decaffeinated composition contains a proprietary mixture of L-theanine (Suntheanine®, standardized at 99%; Taiyo International, Minneapolis, Minn.), and epigallocatechin gallate (EGCG; Sunphenon®, Taiyo International, Minneapolis, Minn., standardized at 50%). The placebo capsules contained microcrystalline cellulose, dextrose, dicalcium phosphate, magnesium stearate, silicon dioxide, FD&C red #40, yellow #6, and blue #1. Each participant was given a bottle containing 180 capsules and was instructed to take 2 capsules every day (one in the morning and one in the evening, preferably with meals) for 12 weeks.

Subjects were given an exit questionnaire. The exit questionnaire included questions to determine if subjects experienced any side effects and/or experienced any changes in feelings of stress or anxiety, or took any additional dietary supplements during the study. Finally, subjects were asked to report whether they thought they had taken the active or the placebo capsules.

Blood collection. Blood was obtained from fasting subjects on Days 0 (baseline), and 21. Blood was collected into one 10 mL sodium heparin tubes for peripheral blood mononuclear cell (PBMC) separation, and one 10 mL SST ™ tube (Vacutainer, Becton Dickinson, Franklin Lakes, N.J.) for serum. Tubes for PBMC were maintained at room temperature (RT), while tubes for serum were kept at 4° C. All tubes were processed within 1 hr of blood collection. Blood cell separation and culture procedures were carried out under sterile conditions.

Serum collection and treatment. Serum was removed from SST ™ tubes after centrifugation (100 g, 10 min, 4° C.) and frozen at −80° C.

Lipid Assays.

Serum Amyloid Alpha (SAA) Assays.

Statistical Analysis. Statistical analysis was carried out using 2-way ANOVA.

Results

Study Subjects. One hundred and twenty-four subjects were enrolled in the study. Six subjects withdrew from the study (three Camellia sinensis composition; CSC, and three placebo). Adverse events were mild, infrequent, and transient. Bloating, gastric upset, dizziness, skin rash, and constipation were reported, and were not different between experimental and control groups. Two subjects taking CSC withdrew with mild skin rashes. One subject said she thought the rash was related to a seafood allergy, and the other thought it might be from the capsule. Neither subject sought medical attention. Such food allergies for green tea have been described previously, mostly in tea factory workers, and the causative agent in green tea is EGCG [33]. However, other reports in the literature describe EGCG as beneficial for asthma and atopic dermatitis [34, 35].

One placebo subject withdrew due to an unrelated urinary tract infection. One placebo individual withdrew because traveling interfered. One placebo individual withdrew because he could not return. One placebo subject withdrew because he just stopped taking the capsules (Table 1). Five more subjects (two CSC and three placebo) were excluded from all data because they were less than 70% compliant. Two more subjects (one CSC and one placebo) were excluded when they reported in their logs that they were ill when the study began, which was an exclusion criterion. Fifty-six subjects in the supplement group and 55 subjects in the placebo group completed the study with 70% or greater compliance, and their data were included in all results and analyses.

Demographics. Average age, gender and BMI values did not differ between experimental and control groups. Subjects were adequately blinded, as there was no difference between CSC and placebo in the percentage of subjects who guessed which treatment to which they were assigned (Table 2).

Ingestion of Camellia sinensis composition (CSC) reduced systolic and diastolic blood pressure. Blood pressure was taken at baseline, three weeks, and three months. After three weeks, there was a decrease in systolic blood pressure (SBP) of 4.2 (P=0.004) and 0.7 (P=0.818) mm Hg in subjects taking CSC, and placebo, respectively. Similarly, there was a decrease in diastolic blood pressure (DBP) of 4.2 (P=0.001) and 1.3 (P=0.107) mm Hg in subjects taking CSC, and placebo, respectively. Thus, subjects taking CSC, but not placebo, had a moderate, statistically significant decrease in both SBP and DBP after three weeks.

After three months, there was a decrease in SBP of 2.8 (P=0.033) and 0.5 (P=0.740) mm Hg in subjects taking CSC, and placebo, respectively. There was a decrease in DBP of 1.3 (P=0.107), and an increase of 1.7 (P=0.018) mm Hg in subjects taking CSC, and placebo, respectively. Thus, blood-pressure lowering effects of CSC were sustained over a three month period, though diminished compared to the effect at three weeks.

Ingestion of Camellia sinensis composition (CSC) decreased LDL cholesterol in subjects with elevated LDL cholesterol. Lipid assays were run for subjects at baseline and at three weeks into the study. There were no significant effects of CSC on total cholesterol, HDL cholesterol, and triglycerides. There were no significant gender-related effects detected (Table 3). In contrast, among subjects with baseline LDL cholesterol >99 mg/dl, there was, compared to placebo, a statistically significant 11.7 mg/dl decrease in LDL cholesterol in subjects taking CSC after three weeks. Subjects with BMI>24.9 experienced a 4.0 mg/dl fall in LDL cholesterol.

Figure 3:
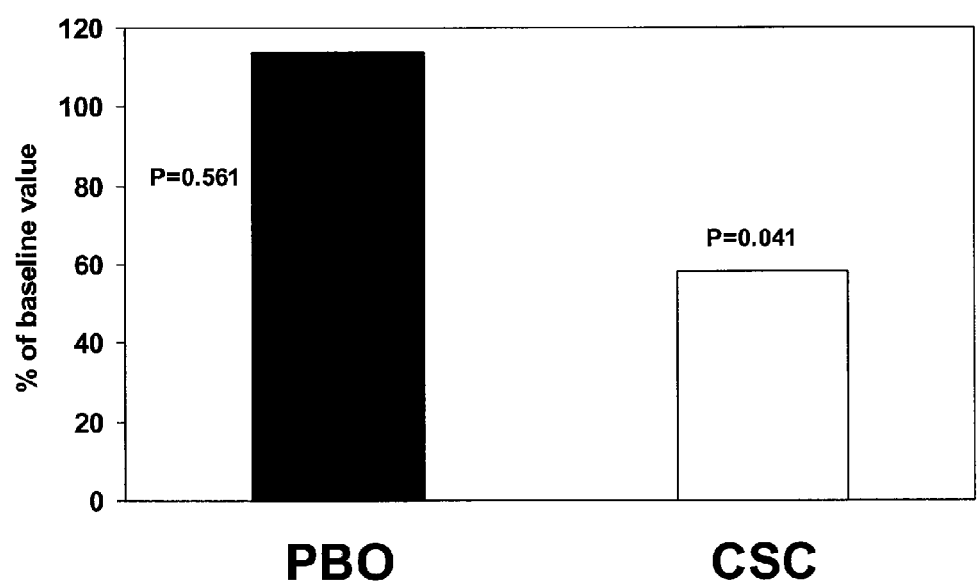
FIG. 3. Change in serum amyloid alpha (SAA). SAA was measured before and either three weeks or three months after taking either CSC (Camellia sinensis composition) or placebo (PBO). Values are expressed as percent change from baseline.

Ingestion of Camellia sinensis composition (CSC) decreased serum amyloid alpha (SAA) levels. To determine the effect of CSC on SAA, a marker of inflammation that is a crucial independent risk factor for CVD, SAA levels at baseline and three weeks after beginning CSC or placebo were compared. Our data show that SAA was reduced by 42% (P=0.041) in subjects taking CSC in just three weeks; in contrast those taking placebo had SAA that increased by 14% (P=0.561; FIG. 3). Furthermore, FIG. 4 shows that administration of CSC also resulted in a reduction of age-related SAA increases.

DISCUSSION

Fewer than 5% of Americans eat the nine servings per day of fruits and vegetables suggested by the latest USDA guidelines released in 2005 [36]. Only 20% of Americans drink any tea at all, while those who do only drink an average of one to two cups per day. Unfortunately, most health benefits from tea are associated with higher amounts of daily consumption [1]. Tea is a vegetable infusion, containing antioxidants and other beneficial nutrients such as L-theanine. Numerous observational studies suggest that tea drinking is beneficial to health, but negative studies have introduced controversy surrounding its health benefits. Though any two studies can yield different results, the conflict between negative and positive studies is likely due in large measure to the observational nature of the studies, and differences in tea preparations (see introduction). A randomized, double blind placebo-controlled study has been conducted using a proprietary Camellia sinensis composition (CSC) with defined amounts of L-theanine and EGCG that as closely as possible approximates the ingestion of 10 cups of green tea per day. The strength of this design lies in elimination of subject selection bias inherent in observational studies. Another strength is the elimination of the variability that can be associated with tea varieties and tea beverage preparations. The present report communicates the results of lipid and inflammatory marker assays performed on frozen serum samples obtained at three weeks into the study.

The results show that the ingestion of two CSC capsules daily over three weeks reduces blood pressure, LDL cholesterol, and chronic inflammation as measured by SAA. The mode of blood pressure reduction may involve several mechanisms. Interestingly, neither L-theanine nor EGCG separately or in combination has been shown to reduce blood pressure in humans. L-theanine reduces blood pressure in spontaneously hypertensive rats by an unknown mechanism [11, 12]. In humans, L-theanine acts on the central nervous system, generating brain α-waves reflective of a relaxed, yet alert state [37]. L-theanine also counteracts the stimulatory effects of caffeine [38]. Hypertension is associated with increased oxidative stress [39]. The combination of EGCG and L-theanine synergistically work together to decrease blood pressure.

It has become apparent that drinking tea is associated with reduced LDL cholesterol (see introduction), but the present study is the first to demonstrate such an effect with encapsulated tea components of defined composition. This moderate, yet significant reduction in LDL cholesterol of 11 mg/dl was achieved in only three weeks. Further study is needed to determine if this LDL lowering effect might be greater after a longer period of time.

Inflammation, as measured by CRP and SAA, has emerged as an important independent CVD risk factor. Reduction of these inflammatory markers by statin drugs prevents progression of CVD even in those subjects with low LDL cholesterol, or in whom LDL cholesterol levels are not reduced by statin therapy [21-23, 40-42]. Recently, tea drinking was associated with reductions in CRP and SAA [24, 25]. Our data show that SAA is reduced by 42% in subjects taking CSC in just three weeks; in contrast those taking placebo had SAA that increased slightly.

It should be noted that the design of the original study was to clinical outcomes regarding upper respiratory illness at three months, and immune function at three weeks (Rowe et al, in press), so blood samples were not drawn at three months. The study was comprised of only healthy adult subjects, so it was not possible to assess the effect of CSC on children, or subjects with chronic illnesses who have increased susceptibility to CVD.

The inventors believe that CSC is a good option for people who have high blood pressure, elevated LDL cholesterol, elevated markers of inflammation, or a combination of these three CVD risk factors. CSC alone may be sufficient for those with mild-to-moderate elevations in these risk factors, but most likely not for those with severe elevations. It has potential as adjunct therapy for those taking prescription medications, and may be particularly useful for those who cannot tolerate statins. CSC's potential for adverse interaction with statins, anti-hypertensives, NSAIDs, and immunosuppressive drugs is low.

This proprietary *Camellia sinensis* composition (CSC) is a safe and effective supplement for reducing blood pressure, LDL cholesterol, and chronic inflammation. Widespread use of this CSC could have enormous beneficial effects in decreasing morbidity in healthy populations.

CSC, *Camellia sinensis* composition; EGCG, epigallocatechin gallate; PBMC, peripheral blood mononuclear cells; CVD, cardiovascular disease; NSAIDs, non-steroidal anti-inflammatory drugs.

REFERENCES

1. Cabrera C, Artacho R, Gimenez R: Beneficial effects of green tea—a review. J Am Coll Nutr 25(2): 79-99; 2006
2. Chung F L, Schwartz J, Herzog C R, Yang Y M: Tea and cancer prevention: studies in animals and humans. J Nutr 133(10): 3268S-3274S; 2003
3. Michels K B, Willett W C, Fuchs C S, Giovannucci E: Coffee, tea, and caffeine consumption and incidence of colon and rectal cancer. J Natl Cancer Inst 97(4): 282-292;
4. Jordan S J, Purdie D M, Green A C, Webb P M: Coffee, tea and caffeine and risk of epithelial ovarian cancer. Cancer Causes Control 15(4): 359-365; 2004
5. Graham H N: Green tea composition, consumption, and polyphenol chemistry. Preventive Medicine 21(3): 334-350; 1992
6. Nichol K L, D'Heilly S, Ehlinger E: Colds and influenza-like illnesses in university students: impact on health, academic and work performance, and health care use. Clin Infect Dis 40(9): 1263-1270; 2005
7. Lorenz M, Jochmann N, von Krosigk A, et al.: Addition of milk prevents vascular protective effects of tea. Eur Heart J 2007
8. Tewari S, Gupta V, Bhattacharya S: Comparative study of antioxidant potential of tea with and without additives. Indian J Physiol Pharmacol 44(2): 215-219; 2000
9. Hodgson J M, Puddey I B, Burke V, Beilin L J, Jordan N: Effects on blood pressure of drinking green and black tea. J Hypertens 17(4): 457-463; 1999
10. Laurie S A, Miller V A, Grant S C, Kris M G, Ng K K: Phase I study of green tea extract in patients with advanced lung cancer. Cancer Chemother Pharmacol 55(1): 33-38; 2005
11. Yokogoshi H, Kato Y, Sagesaka Y M, Takihara M T, Kakuda T, Takeuchi N: Reduction effect of theanine on blood pressure and brain 5-hydroxyindoles in spontaneously hypertensive rats. Bioscience, Biotechnology & Biochemistry 59(4): 615-618; 1995
12. Yokogoshi H, Kobayashi M: Hypotensive effect of gamma-glutamylmethylamide in spontaneously hypertensive rats. Life Sci 62(12): 1065-1068; 1998
13. Yokozawa T, Oura H, Nakagawa H, Sakanaka S, Kim M: Effects of a component of green tea on the proliferation of vascular smooth muscle cells. Bioscience, Biotechnology & Biochemistry 59(11): 2134-2136; 1995
14. Maron D J, Lu G P, Cai N S, et al.: Cholesterol-lowering effect of a theaflavin-enriched green tea extract: a randomized controlled trial. Arch Intern Med 163(12): 1448-1453;
15. Davies M J, Judd J T, Baer D J, et al.: Black tea consumption reduces total and LDL cholesterol in mildly hypercholesterolemic adults. J Nutr 133(10): 3298S-3302S; 2003
16. Bingham S A, Vorster H, Jerling J C, et al.: Effect of black tea drinking on blood lipids, blood pressure and aspects of bowel habit. Br J Nutr 78(1): 41-55; 1997
17. Coimbra S, Alice Santos-Silvaa, Petronila Rocha-Pereirab, Susana Rochaa, Elisabeth Castro: Green tea consumption improves plasma lipid profiles in adults. Nutrition Research 26: 607-607; 2006
18. Erba D, Riso P, Bordoni A, Foti P, Biagi P L, Testolin G: Effectiveness of moderate green tea consumption on antioxidative status and plasma lipid profile in humans. J Nutr Biochem 16(3): 144-149; 2005
19. Bursill C, Roach P D, Bottema C D, Pal S: Green tea upregulates the low-density lipoprotein receptor through the sterol-regulated element binding Protein in HepG2 liver cells. J Agric Food Chem 49(11): 5639-5645; 2001
20. Abe I, Seki T, Umehara K, et al.: Green tea polyphenols: novel and potent inhibitors of squalene epoxidase. Biochem Biophys Res Commun 268(3): 767-771; 2000
21. Johnson B D, Kip K E, Marroquin O C, et al.: Serum amyloid A as a predictor of coronary artery disease and cardiovascular outcome in women: the National Heart, Lung, and Blood Institute-Sponsored Women's Ischemia Syndrome Evaluation (WISE). Circulation 109(6): 726-732; 2004
22. Jousilahti P, Salomaa V, Rasi V, Vahtera E, Palosuo T: The association of c-reactive protein, serum amyloid a and fibrinogen with prevalent coronary heart disease—baseline findings of the PAIS project. Atherosclerosis 156(2): 451-456; 2001
23. Danesh J, Whincup P, Walker M, et al.: Low grade inflammation and coronary heart disease: prospective study and updated meta-analyses. Bmj 321(7255): 199-204; 2000
24. Steptoe A, Gibson E L, Vuononvirta R, et al.: The effects of chronic tea intake on platelet activation and inflammation: A double-blind placebo controlled trial. Atherosclerosis 2006
25. De Bacquer D, Clays E, Delanghe J, De Backer G: Epidemiological evidence for an association between habitual tea consumption and markers of chronic inflammation. Atherosclerosis 189(2): 428-435; 2006

26. Porath D, Riegger C, Drewe J, Schwager J: Epigallocatechin-3-gallate impairs chemokine production in human colon epithelial cell lines. J Pharmacol Exp Ther 315(3): 1172-1180; 2005
27. August D A, Landau J, Caputo D, Hong J, Lee M J, Yang C S: Ingestion of green tea rapidly decreases prostaglandin E2 levels in rectal mucosa in humans. Cancer Epidemiol Biomarkers Prev 8(8): 709-713; 1999
28. Yuan G J, Gong Z J, Sun X M, Zheng S H, Li X: Tea polyphenols inhibit expressions of iNOS and TNF-alpha and prevent lipopolysaccharide-induced liver injury in rats. Hepatobiliary Pancreat Dis Int 5(2): 262-267; 2006
29. Kawai K, Tsuno N H, Kitayama J, et al.: Epigallocatechin gallate attenuates adhesion and migration of CD8+ T cells by binding to CD11b. J Allergy Clin Immunol 113(6): 1211-1217; 2004
30. Singh R, Ahmed S, Malemud C J, Goldberg V M, Haqqi T M: Epigallocatechin-3-gallate selectively inhibits interleukin-1beta-induced activation of mitogen activated protein kinase subgroup c-Jun N-terminal kinase in human osteoarthritis chondrocytes. J Orthop Res 21(1): 102-109; 2003
31. Handa O, Naito Y, Takagi T, et al.: Inhibitory effects of catechins on neutrophil-dependent gastric inflammation. Redox Rep 7(5): 324-328; 2002
32. Nantz M P, Rowe C A, Nieves C, Jr., Percival S S: Immunity and antioxidant capacity in humans is enhanced by consumption of a dried, encapsulated fruit and vegetable juice concentrate. J Nutr 136(10): 2606-2610; 2006
33. Shirai T, Hayakawa H, Akiyama J, et al.: Food allergy to green tea. J Allergy Clin Immunol 112(4): 805-806; 2003
34. Kim S H, Park H J, Lee C M, et al.: Epigallocatechin-3-gallate protects toluene diisocyanate-induced airway inflammation in a murine model of asthma. FEBS Lett 580(7): 1883-1890; 2006
35. Hisano M, Yamaguchi K, Inoue Y, et al.: Inhibitory effect of catechin against the superantigen staphylococcal enterotoxin B (SEB). Arch Dermatol Res 295(5): 183-189;
36. Committee DGA: Dietary guidelines for Americans, 2005. Washington, D.C.: USDA, 2005.
37. Kobayashi K Y N, Nobuyuki Aoi, Lekh Raj Juneja, Mujo Kim, Takehiko Yamamoto, and Sukeo Sugimoto: Effects of L-theanine on the Release of Alpha-Brain Waves in Human Volunteers. Nippon Noegikagaku Kaishi 72: 153-157;
38. Kakuda T, Nozawa A, Unno T, Okamura N, Okai O: Inhibiting effects of theanine on caffeine stimulation evaluated by EEG in the rat. Biosci Biotechnol Biochem 64(2): 287-293; 2000
39. Xu S, Touyz R M: Reactive oxygen species and vascular remodelling in hypertension: still alive. Can J Cardiol 22(11): 947-951; 2006
40. Ridker P M, Rifai N, Clearfield M, et al.: Measurement of C-reactive protein for the targeting of statin therapy in the primary prevention of acute coronary events. N Engl J Med 344(26): 1959-1965; 2001
41. Ridker P M, Stampfer M J, Rifai N: Novel risk factors for systemic atherosclerosis: a comparison of C-reactive protein, fibrinogen, homocysteine, lipoprotein(a), and standard cholesterol screening as predictors of peripheral arterial disease. Jama 285(19): 2481-2485; 2001
42. Ridker P M, Cannon C P, Morrow D, et al.: C-reactive protein levels and outcomes after statin therapy. N Engl J Med 352(1): 20-28; 2005

TABLE 1

Study withdrawals

| Subject # | Treatment | Capsules Consumed For | Reason for Withdrawal |
|---|---|---|---|
| 2 | supplement | 11 d | Facial & chest rash, itching, red/watery eyes, puffy eyes, congestion) |
| 30 | placebo | ? | Unable to return |
| 43 | supplement | On & off 20 dy (?) | Hives 3× |
| 45 | placebo | 32 dy | Traveling interfered |
| 60 | placebo | 1 mo (?) | Urinary tract infection |
| 116 | placebo | ? | Discontinued taking capsules |
| 119 | placebo | 1 mo (?) | Capsules upsetting stomach |

TABLE 2

Demographics of the study population at baseline

| | Supplement | Placebo | P value |
|---|---|---|---|
| Age | 28.9 ± 1.07 | 30.3 ± 1.5 | 0.65 |
| Gender male | 20 | 23 | |
| Gender female | 32 | 33 | |
| Height (m) | 1.7 ± 0.01 | 1.7 ± 0.01 | 0.60 |
| Weight (kg) | 74.9 ± 1.7 | 73.3 ± 2.0 | 0.67 |
| BMI | 25.4 ± 0.6 | 24.3 ± 0.8 | 0.94 |
| Compliance (%) | 93% ± 7 | 93% ± 7 | 0.56 |
| Blinding (% guessed correctly) | 50 | 48 | 1.0 |
| Systolic BP[1] | 130 ± 0.92 | 129.7 ± 0.84 | 0.76 |
| Diastolic BP[1] | 80.2 ± 0.56 | 78.3 ± 0.51 | 0.65 |
| Total Cholesterol[2] | 178.1 ± 1.74 | 175.8 ± 1.68 | 0.70 |
| SAA[2] | 31.79 ± 4.6 | 26.25 ± 4.4 | 0.60 |

[1]Values are expressed as mm Hg ± SEM
[2]Values are expressed as mg/dl ± SEM

TABLE 3

Differences in Serum Lipids Before and After CSC or PBO

| | Total cholesterol | | LDL cholesterol | | HDL cholesterol | | Triglycerides | |
|---|---|---|---|---|---|---|---|---|
| | CSC | PBO | CSC | PBO | CSC | PBO | CSC | PBO |
| All | −3.08 ± 2.47 (52) | 0.46 ± 2.34 (56) | −2.35 ± 2.4[1] | 3.09 ± 2.0 | −0.09 ± 0.83 | −0.78 ± 0.86 | −2.92 ± 6.12 | −8.80 ± 5.90 |
| BMI >24.9 | −5.86 ± 4.25 (22) | 3.31 ± 4.12 (22) | −4.0 ± 4.2[2] | 7.64 ± 2.41 | −0.86 ± 1.4 | 0.14 ± 1.5 | −4.64 ± 12.5 | −22.2 ± 11.5 |
| Chol >199 | −9.70 ± 8.74 (10) | −9.75 ± 4.82 (12) | −10.2 ± 7.8 | −2.33 ± 4.1 | −0.7 ± 1.6 | −1.0 ± 1.6 | 6.6 ± 12.9 | −31.5 ± 19.9 |
| LDL >99 | −10.61 ± 5.51 (18) | −1.63 ± 3.80 (24) | −11.7 ± 4.9[3] | 1.88 ± 3.0 | −0.06 ± 1.0 | 0.13 ± 1.0 | 5.9 ± 7.8 | −17.3 ± 10.5 |

TABLE 3-continued

Differences in Serum Lipids Before and After CSC or PBO

| | Total cholesterol | | LDL cholesterol | | HDL cholesterol | | Triglycerides | |
|---|---|---|---|---|---|---|---|---|
| | CSC | PBO | CSC | PBO | CSC | PBO | CSC | PBO |
| Men | −9.91 ± 3.80 (21) | −3.73 ± 3.53 (23) | −7.43 ± 3.10 | −0.73 ± 3.2 | −0.71 ± 1.18 | 0.46 ± 0.95 | −8.6 ± 9.9 | −14.6 ± 7.9 |
| Women | 1.55 ± 3.0 (31) | −3.24 ± 3.1 (33) | 1.09 ± 3.16 | 5.64 ± 2.50 | 0.32 ± 1.16 | −1.33 ± 1.29 | 0.9 ± 7.8 | −4.9 ± 8.3 |

Numbers in parentheses are N in each group. CSC, *Camellia sinensis* formula; PBO, placebo. Values are expressed as mg/dl ± SEM.
[1] $p = 0.086$ compared to placebo
[2] $p = 0.038$ compared to placebo
[3] $p = 0.017$ compared to placebo While the principles of the invention have been made clear in illustrative embodiments, there will be immediately apparent to those skilled in the art, in view of the teachings herein, many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

The references referred to herein are incorporated herein in their entirety to the extent they are not inconsistent with the teachings herein.

What is claimed is:

1. A method of lowering blood pressure, lowering low density lipoprotein cholesterol levels, and lowering serum amyloid alpha levels in a patient in need thereof consisting essentially of orally administering to the patient an admixture of 75-300 mg of L-theanine in the total admixture and 75-250 mg of EGCG in the total admixture.

\* \* \* \* \*